US008632599B1

(12) United States Patent
Bonitati et al.

(10) Patent No.: US 8,632,599 B1
(45) Date of Patent: Jan. 21, 2014

(54) KNEE PROSTHESIS SYSTEM WITH SIDE-MOUNTED AUGMENTS

(75) Inventors: John A Bonitati, Warsaw, IN (US); Tyler S Hathaway, Auburn, IN (US)

(73) Assignee: Depuy (Ireland), Co Cork (IE)

( * ) Notice: Subject to any disclaimer, the term of this patent is extended or adjusted under 35 U.S.C. 154(b) by 0 days.

(21) Appl. No.: 13/539,796

(22) Filed: Jul. 2, 2012

(51) Int. Cl.
*A61F 2/38* (2006.01)
(52) U.S. Cl.
USPC ..................................... 623/20.16; 623/20.35
(58) Field of Classification Search
USPC .................................. 623/20.16, 20.35, 23.28
See application file for complete search history.

(56) References Cited

U.S. PATENT DOCUMENTS

| | | | | |
|---|---|---|---|---|
| 4,936,847 A | * | 6/1990 | Manginelli | ................ 623/20.16 |
| 5,571,194 A | * | 11/1996 | Gabriel | ...................... 623/20.16 |
| 5,776,201 A | * | 7/1998 | Colleran et al. | .......... 623/20.15 |
| 5,984,969 A | * | 11/1999 | Matthews et al. | .......... 623/20.11 |
| 6,005,018 A | | 12/1999 | Cicierega et al. | |
| 7,175,665 B2 | | 2/2007 | German et al. | |
| 2003/0204267 A1 | | 10/2003 | Hazebrouck et al. | |

OTHER PUBLICATIONS

DePuy PFC Sigma RP, "PFC Sigma Knee System with Rotating Platform Technical Monograph", 1999, Section 8, pp. 8.1 through 8.6, 0611-29-050 (Rev. 3), 10 Pages.

* cited by examiner

*Primary Examiner* — David H Willse
*Assistant Examiner* — Javier Blanco

(57) ABSTRACT

A modular knee prosthesis system comprises a distal femoral articulation component, a distal augment, a posterior augment and a first connector for securing at least one of the augments to the distal femoral articulation component through a bore in the augment and an opening in the distal femoral articulation component. The distal femoral articulation component has a distal bone-facing surface, a posterior bone-facing surface and an opening. The openings into the bores of the augments are in the medial or lateral side surface of the augment. Both augments can be mounted and removed from the distal femoral articulation component from either the medial or lateral side.

11 Claims, 14 Drawing Sheets

KNEE PROSTHESIS SYSTEM WITH SIDE-MOUNTED AUGMENTS

TECHNICAL FIELD

The present disclosure relates generally to prosthetic joints, and more particularly to a modular prosthetic knee joint system that includes augments.

BACKGROUND

The knee joint basically consists of the bone interface of the distal end of the femur and the proximal end of the tibia. Appearing to cover or at least partially protect this interface is the patella, which is a sesamoid bone within the tendon of the long muscle (quadriceps) on the front of the thigh. This tendon inserts into the tibial tuberosity and the posterior surface of the patella is smooth and glides over the femur.

The femur is configured with two knob like processes (the medial condyle and the lateral condyle) which are substantially smooth and which articulate with the medial plateau and the lateral plateau of the tibia, respectively. The plateaus of the tibia are substantially smooth and slightly cupped thereby providing a slight receptacle for receipt of the femoral condyles.

When the knee joint is damaged whether as a result of an accident or illness, a prosthetic replacement of the damaged joint may be necessary to relieve pain and to restore normal use to the joint. Typically the entire knee joint is replaced by means of a surgical procedure that involves removal of the surfaces of the corresponding damaged bones and replacement of these surfaces with prosthetic implants. This replacement of a native joint with a prosthetic joint is referred to as a primary total-knee arthroplasty.

On occasion, the primary knee prostheses fails. Failure can result from many causes, including wear, aseptic loosening, osteolysis, ligamentous instability, arthrofibrosis and patellofemoral complications. When the failure is debilitating, revision knee surgery may be necessary. In a revision, the primary knee prosthesis is removed and replaced with components of a revision prosthetic knee system.

Knee implant systems for both primary and revision applications are available from a variety of manufacturers, including DePuy Orthopaedics, Inc. of Warsaw, Ind. DePuy and others offer several different systems for both primary and revision applications. For example, DePuy Orthopaedics offers the P.F.C. SIGMA® Knee System, the LCS® Total Knee System, and the S-ROM Modular Total Knee System. Each of these orthopaedic knee systems includes several components, some appropriate for use in primary knee arthroplasty and some appropriate for use in revision surgery.

DePuy Orthopaedics also offers other orthopaedic implant systems for other applications. One such system is the LPS System. The LPS System is provided for use in cases of severe trauma and disease. In such cases, the trauma or disease can lead to significant amounts of bone loss. The LPS System provides components that can replace all or significant portions of a particular bone, such as the femur. The DePuy LPS System is described more fully in U.S. patent application Ser. No. 10/135,791, entitled "Modular Limb Preservation System", filed Apr. 30, 2002 by Hazebrouck et al., which is incorporated by reference herein in its entirety.

In some patients, bone deficiencies in the distal and posterior femur may make it difficult for the surgeon to re-establish the natural joint line and to provide equal flexion and extension gaps. Prosthetic knee implant systems have commonly included femoral augments for use on the distal and posterior bone-facing surfaces of the femoral implant components. Examples of such augments are disclosed in U.S. Pat. Nos. 6,005,018 and 5,984,969, which are incorporated by reference herein in their entireties. Such components serve to augment the inferior and posterior portions of the femoral component to add additional thickness to compensate for the lack of sufficient boney tissue, allowing the joint line to be distalized.

As disclosed in U.S. Pat. Nos. 6,005,018 and 5,984,969, such augments are commonly connected to the bone-facing surfaces of the distal femoral articulation components through screws or pins inserted superiorly or anteriorly from the bone-facing surfaces of the augments and threaded into threaded openings or collets or other receptacles received in openings in the bone-facing surface of the distal femoral articulation components. For the posterior augments, a special tool may be required to connect the augment to the posterior condylar bone-facing surface of the distal femoral articulation component; for example, a wobble driver tip to facilitate access across the femoral anterior flange.

After the augmented distal femoral articulation component is implanted, the augments and distal femoral articulation components cannot be disassembled until after the entire assembly is removed from the distal femur because the connection mechanisms are no longer accessible. During revision surgery, it may be advantageous to the surgeon to have the option of severing the connections between the distal femoral articulation component and the augments prior to removal of these components from the bone.

SUMMARY

The present invention provides a modular knee implant system that allows the surgeon to separate distal femoral articulation components and augments from an implanted assembly prior to removal of the assembly from the bone. The modular knee implant system of the present invention also allows for quick and simple connection of augments to distal femoral articulation components.

According to one aspect of the present disclosure, a modular knee prosthesis system is provided. The system includes a distal femoral articulation component, an augment and a first connector for securing the augment to the distal femoral articulation component. The distal femoral articulation component has a pair of curved distal condylar articulating surfaces, a pair of curved posterior condylar articulating surfaces, a distal bone-facing surface and a posterior bone-facing surface. The augment is sized and shaped to be received on one of the bone-facing surfaces of the distal femoral articulation component. The augment includes a first surface, a second surface spaced from and generally opposite to the first surface, side surfaces extending between and connecting the first surface and the second surface, and a body between the first and second surface. At least one of the side surfaces has an opening into a bore extending from the side surface through the body and through another surface of the augment. The distal femoral articulation component has an opening to receive the connector to selectively mount the augment to the distal femoral articulation component.

In an illustrative embodiment, the bore of the augment has a central longitudinal axis that defines an acute angle with at least one of the first surface and the second surface of the augment.

In a more particular embodiment, the augment is a distal femoral augment, the central longitudinal axis of the bore defines an acute angle with the second surface of the augment and the opening in the distal femoral articulation component is in the distal bone-facing surface of the distal femoral articulation component. In this embodiment, the side surfaces of the augment may include a medial surface and a lateral surface and the opening into the bore may be in one of the medial surface and lateral surface.

In another illustrative embodiment, the bore in the augment has a central longitudinal axis between the first surface and the second surface of the augment.

In a more particular embodiment, the augment is a posterior femoral augment. In this embodiment, the side surfaces of the augment may include a medial surface and a lateral surface and the opening into the bore may be in one of the medial surface and lateral surface. In this embodiment, the distal femoral articulation component may be a posterior stabilized component including a box having a box top wall and a box side wall; the box side wall extends from the box top wall to at least one of the distal bone-facing surface and a posterior bone-facing surface and the opening in the distal femoral articulation component is in the box side wall.

In any of the above embodiments, the connecting element may comprise a screw or bolt.

In any of the above embodiments, the distal bone-facing surface of the distal femoral articulation component may have a recessed distal cement pocket and the posterior bone-facing surface of the distal femoral articulation component may have a recessed posterior cement pocket. The second surface of the augment may include a plurality of protruding feet sized, shaped and positioned to be received in a unique position within one of the cement pockets when the augment is assembled with the distal femoral articulation component to positively locate the augment with respect to the cement pocket. In more particular embodiments, the recessed cement pocket may be tapered so that the pocket is deeper at one end and the feet of the augment may be shaped so that the outermost surfaces of the feet lie in a plane that defines an acute angle with the first surface of the augment.

In any of the above embodiments, the first surface of the augment may have a recessed cement pocket.

According to another aspect of the present invention, a modular knee prosthesis system comprises a distal femoral articulation component, a distal augment, a posterior augment and a first connector for securing at least one of the augments to the distal femoral articulation component through the bore of the augment and the opening in the distal femoral articulation component. The distal femoral articulation component has a pair of curved distal condylar articulating surfaces, a pair of curved posterior condylar articulating surfaces, a distal bone-facing surface, a posterior bone-facing surface and an opening. The distal augment is sized and shaped to be received on the distal bone-facing surface of the distal femoral articulation component and includes a first surface, a second surface spaced from and generally opposite to the first surface and side surfaces extending between and connecting the first surface and the second surface. The distal augment has a body between the first and second surface and at least one of the side surfaces has an opening into a bore extending from the side surface through the body and through another surface of the distal augment. The posterior augment is sized and shaped to be received on the posterior bone-facing surface of the distal femoral articulation component and includes a first surface, a second surface spaced from and generally opposite to the first surface and side surfaces extending between and connecting the first surface and the second surface. The posterior augment has a body between the first and second surfaces and at least one of the side surfaces has an opening into a bore extending from the side surface through the body and through another surface of the posterior augment.

In another particular embodiment, the distal femoral articulation component is a posterior stabilized component including a box having a box top wall and a box side wall, the box side wall extending from the box top wall to at least one of the distal bone-facing surface and a posterior bone-facing surface of the distal femoral articulation component. In this embodiment, the opening in the distal femoral articulation component may be in the box side wall. Moreover, in this embodiment, the bore in at least one of the augments may have a central longitudinal axis between the first surface and the second surface of the posterior augment. Further, in this embodiment, the opening in the box side wall may be positioned and shaped to align with the bore in the augment when the second surface of the augment is mounted on one of the bone-facing surfaces of the distal femoral articulation component. The bore in at least one of the augments may have a central longitudinal axis defining an acute angle with the second surface of that augment. At least one of the bone-facing surfaces of the distal femoral articulation component may have an opening into a bore. This opening may be positioned and shaped to align with the bore in the augment when the second surface of the augment is mounted on one of the bone-facing surfaces of the distal femoral articulation component. In this embodiment, the bore in one of the augments may extend between the side surfaces of the augment and the bore in the other augment may extend from the side surface of the augment to the second surface of the augment. In this embodiment, system may include a second connector that is longer than the first connector.

In any of the above embodiments of this aspect of the invention, the distal bone-facing surface of the distal femoral articulation component may have a recessed distal cement pocket and the posterior bone-facing surface of the distal femoral articulation component may have a recessed posterior cement pocket. The second surface of the distal augment may include a plurality of protruding feet sized, shaped and positioned to be received in a unique position within the distal cement pocket when the distal augment is assembled with the distal femoral articulation component to positively locate the distal augment with respect to the distal cement pocket. The second surface of the posterior augment may also include a plurality of protruding feet sized, shaped and positioned to be received in a unique position within the posterior cement pocket when the posterior augment is assembled with the distal femoral articulation component to positively locate the posterior augment with respect to the posterior cement pocket. In this embodiment, the recessed posterior cement pocket may tapered so that the posterior cement pocket is deeper at one end and the feet of the posterior augment may be shaped so that the outermost surfaces of the feet lie in a plane that defines an acute angle with the first surface of the posterior augment.

In any of the embodiments of this aspect of the invention, the first surface of the distal augment may have a recessed cement pocket and the first surface of the posterior augment may have a recessed cement pocket.

BRIEF DESCRIPTION OF THE DRAWINGS

The detailed description particularly refers to the accompanying figures in which.

DETAILED DESCRIPTION OF THE DRAWINGS

Figure 1:
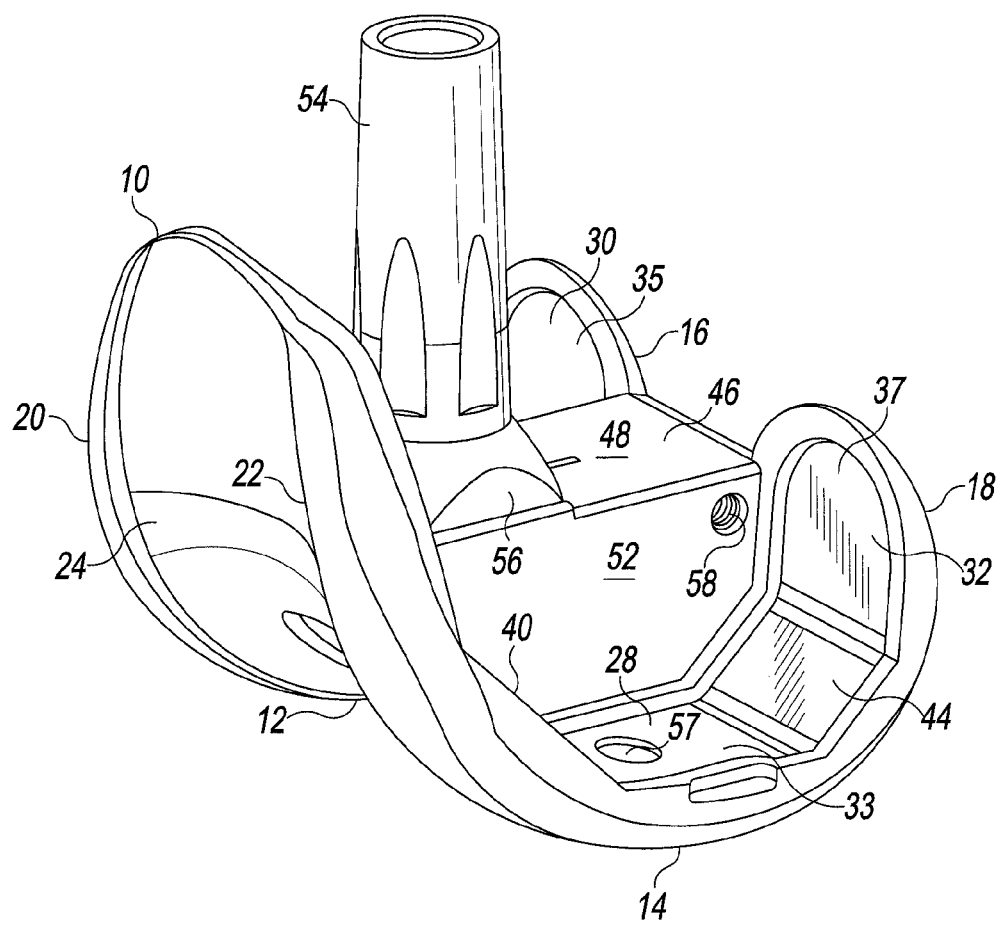
FIG. 1 is a perspective view of a distal femoral articulation component of a modular knee prosthesis system incorporating the principles of the present invention.

While the concepts of the present disclosure are susceptible to various modifications and alternative forms, specific exemplary embodiments thereof have been shown by way of example in the drawings and will herein be described in detail. It should be understood, however, that there is no intent to limit the disclosure to the particular forms disclosed, but on the contrary, the intention is to cover all modifications, equivalents, and alternatives following within the spirit and scope of the invention as defined by the appended claims.

Terms representing anatomical references, such as anterior, posterior, superior, inferior, proximal, distal, etcetera, may be used throughout the specification in reference to the orthopaedic implants described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 2:
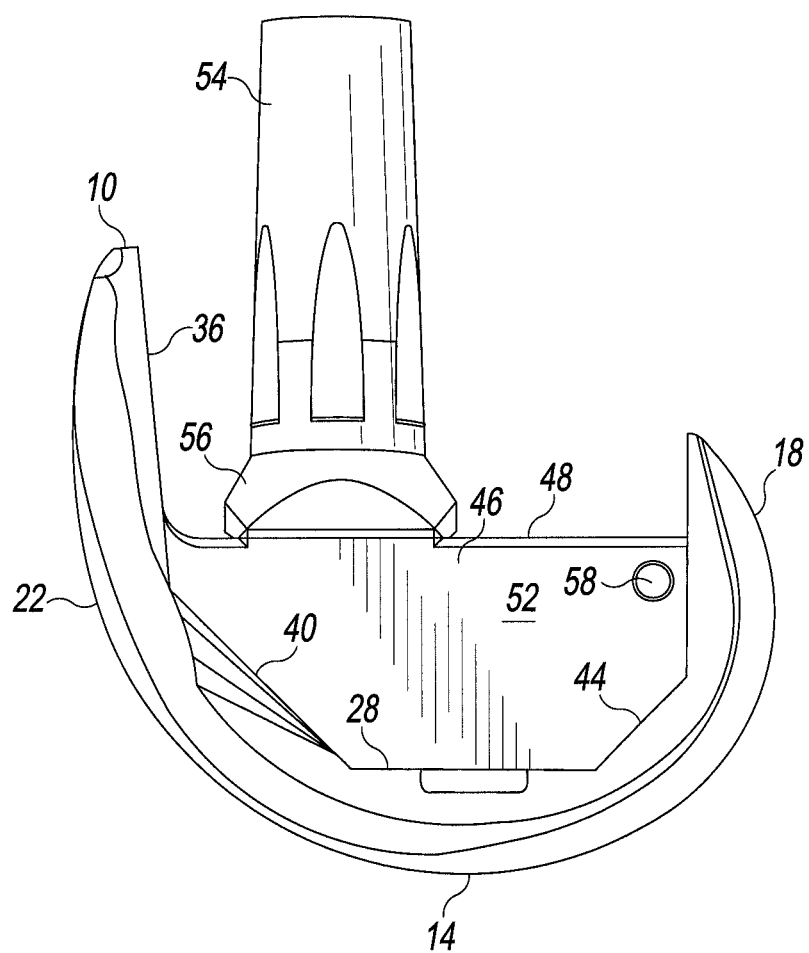
FIG. 2 is a side view of the distal femoral articulation component of FIG. 1.
Figure 3:
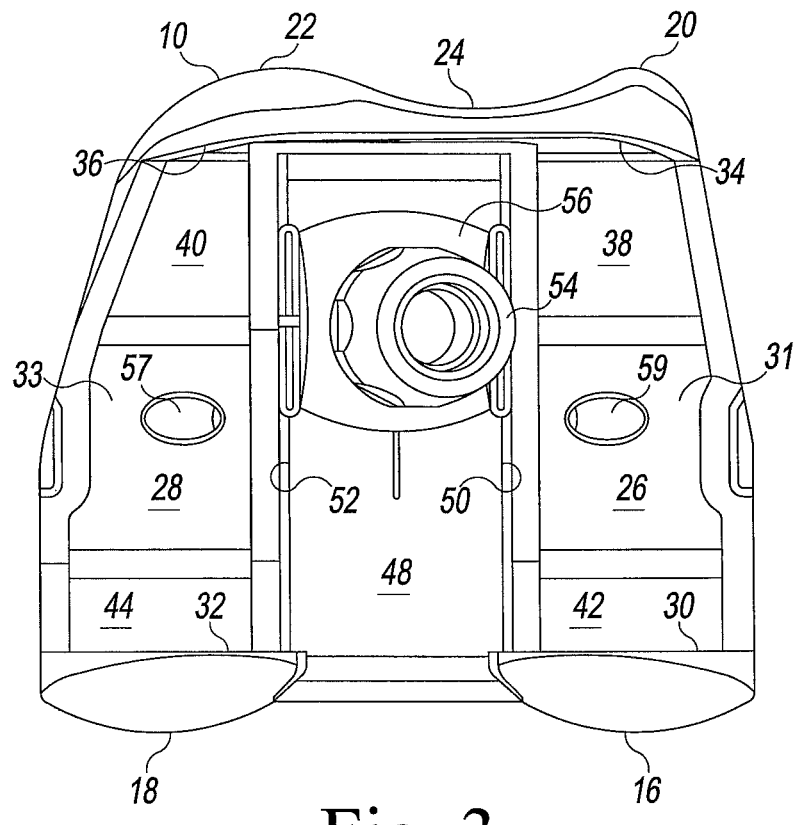
FIG. 3 is a top view of the distal femoral articulation component of FIGS. 1-2.
Figure 4:
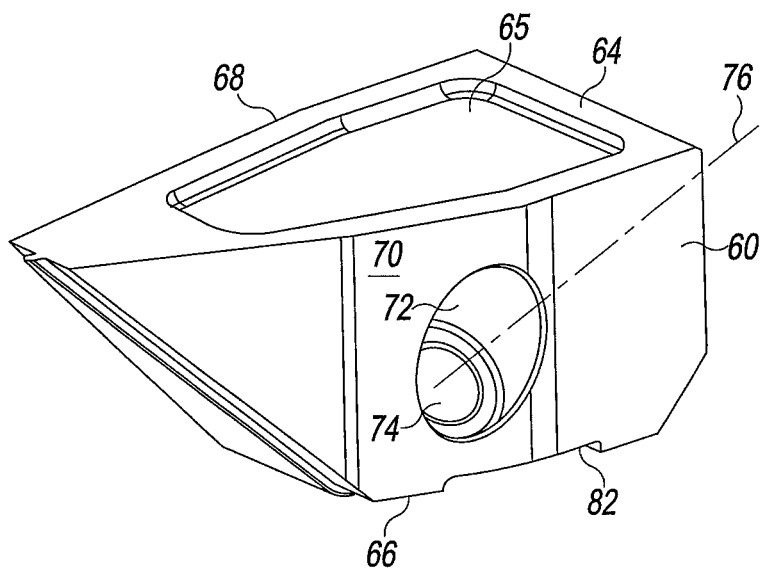
FIG. 4 is a perspective view of a distal augment of a modular knee prosthesis system incorporating the principles of the present invention.
Figure 5:
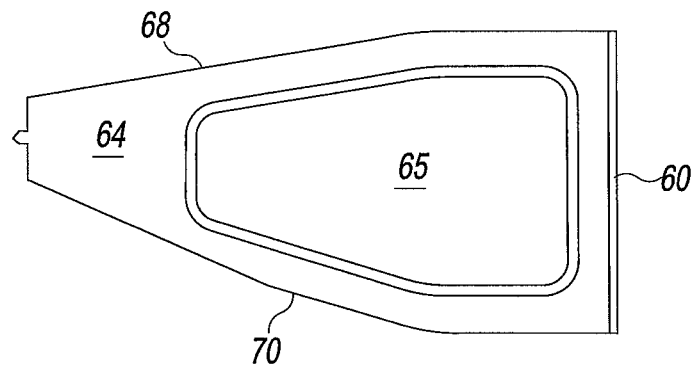
FIG. 5 is a top view of the distal augment of FIG. 4.
Figure 6:
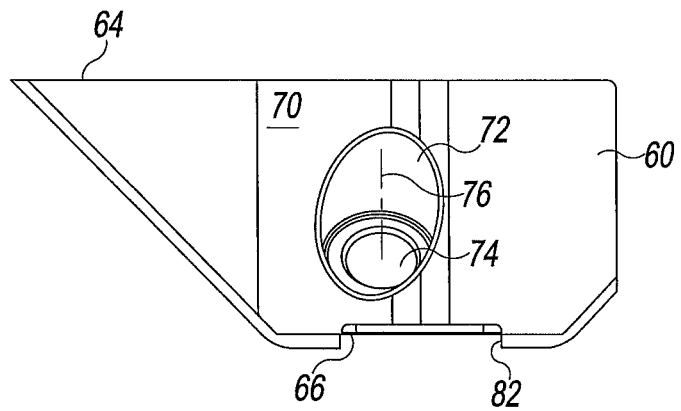
FIG. 6 is a side view of the distal augment of FIGS. 4-5.
Figure 7:
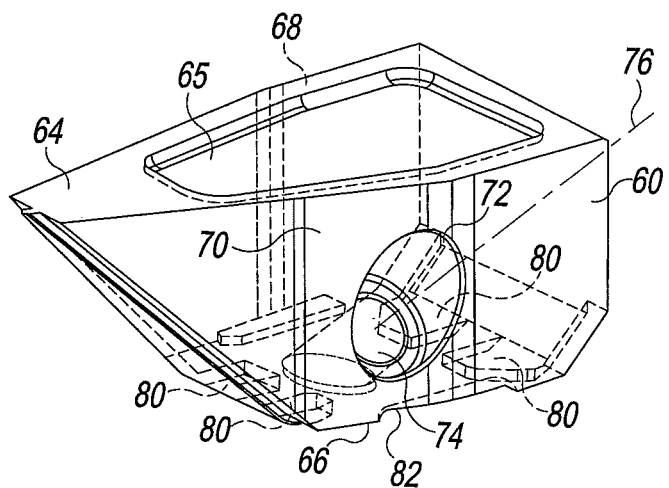
FIG. 7 is a perspective of the distal augment of FIGS. 4-6, with additional features shown in phantom.

FIGS. 1-3 illustrate an example of a distal femoral implant component that may be used with the modular knee prosthesis system of the present invention. The illustrated distal femoral articulation component 10 has a pair of spaced, curved distal articulating surfaces 12, 14 extending posteriorly to a pair of spaced, curved posterior articulating surfaces 16, 18. The distal articulating surfaces 12, 14 extend anteriorly to anterior surfaces 20, 22, which are connected by a patellar groove 24.

The distal femoral articulation component 10 has a plurality of flat bone-facing surfaces opposite the outer articulating surfaces 12, 14, 16, 18, 20, 22, 24. The bone-facing surfaces include flat distal bone-facing surfaces 26, 28, posterior bone-facing surfaces 30, 32, anterior bone-facing surfaces 34, 36 and sets of anterior chamfers 38, 40 and posterior chamfers 42, 44. The anterior chamfers 38, 40 connect the anterior bone-facing surfaces 34, 36 to the distal bone-facing surfaces 26, 28 and the posterior chamfers 42, 44 connect the distal bone-facing surfaces 26, 28 to the posterior bone-facing surfaces 30, 32. All of the illustrated bone-facing surfaces 26, 28, 30, 32, 34, 36, 38, 40, 42, 44 are fixation surfaces, and include recesses to receive bone-cement to bond the distal femoral articulation component 10 to the resected surfaces of the distal femur. The recesses define cement pockets (shown at 33, 35 and 37 in FIGS. 1 and 31 and 33 in FIG. 3) that may have features such as those disclosed in U.S. Pat. Pub. No. 20120083894, entitled "Femoral Component of a Knee Prosthesis Having an Angled Cement Pocket", the disclosure of which is incorporated by reference herein in its entirety. For example, the cement pockets 33, 35 in the posterior bone-facing surfaces 30, 32 may be angled so that the pockets are deeper at their inferior ends than at their superior ends.

The illustrated distal femoral articulation component 10 is a posterior stabilized component intended for use when the posterior cruciate ligament is sacrificed. Accordingly, the illustrated distal femoral articulation component 10 includes a box 46 having a box top wall 48 and box side walls 50, 52 extending from the box top wall 48 to the bone-facing surfaces 26, 28, 30, 32, 34, 36, 38, 40, 42, 44 of the distal femoral articulation component 10.

The illustrated distal femoral articulation component 10 also includes a modular stem 54, along with a collar 56 for placement between the stem 54 and the box top wall 48 and a bolt (not shown) so that the stem 54 and collar 56 may be selectively mounted on the box 46 of the distal femoral articulation component 10. Each stem 54 may have a frusto-conical outer surface that is smooth and tapered for receiving a metaphyseal sleeve and connection structures at the proximal end for connecting a stem extension (not shown) to the stem 54.

The illustrated distal femoral articulation component 10 has bores 57, 58, 59 to receive connectors to selectively assemble with a distal femoral augment 60 and a posterior femoral augment 62. The distal femoral augment 60 is illustrated in FIGS. 4-8 and 15-16 and is sized and shaped to be received on one of the distal bone-facing surfaces 26, 28 of the distal femoral articulation component 10. The posterior femoral augment 62 is illustrated in FIGS. 9-16 and is sized and shaped to be received on one of the posterior bone-facing surfaces 30, 32 of the distal femoral articulation component 10. Both augments 60, 62 are described in more detail below.

The distal femoral augment 60 has a first surface 64, a second surface 66 spaced from and generally opposite to the first surface 64 and side surfaces 68, 70 extending between the first surface 64 and the second surface 66. The distal femoral augment 60 has a body extending between the surfaces 64, 66, 68, 70.

One of the side surfaces 70 of the first illustrated distal femoral augment 60 has an oval-shaped opening 72 into a cylindrical bore 74. The bore 74 extends from the side surface 70, through the body of the augment 60 and out through the second surface 66 of the augment 60. The bore 74 has a central longitudinal axis 76 that defines an acute angle with both the first surface 64 and the second surface 66 of the augment 60. The interior of the cylindrical bore 74 is smooth, and sized to receive the shaft of a first connector 78. In the illustrated embodiment, the first connector 78 comprises a screw or bolt, although other connectors, such as a pin and collet, could be used.

Figure 8:
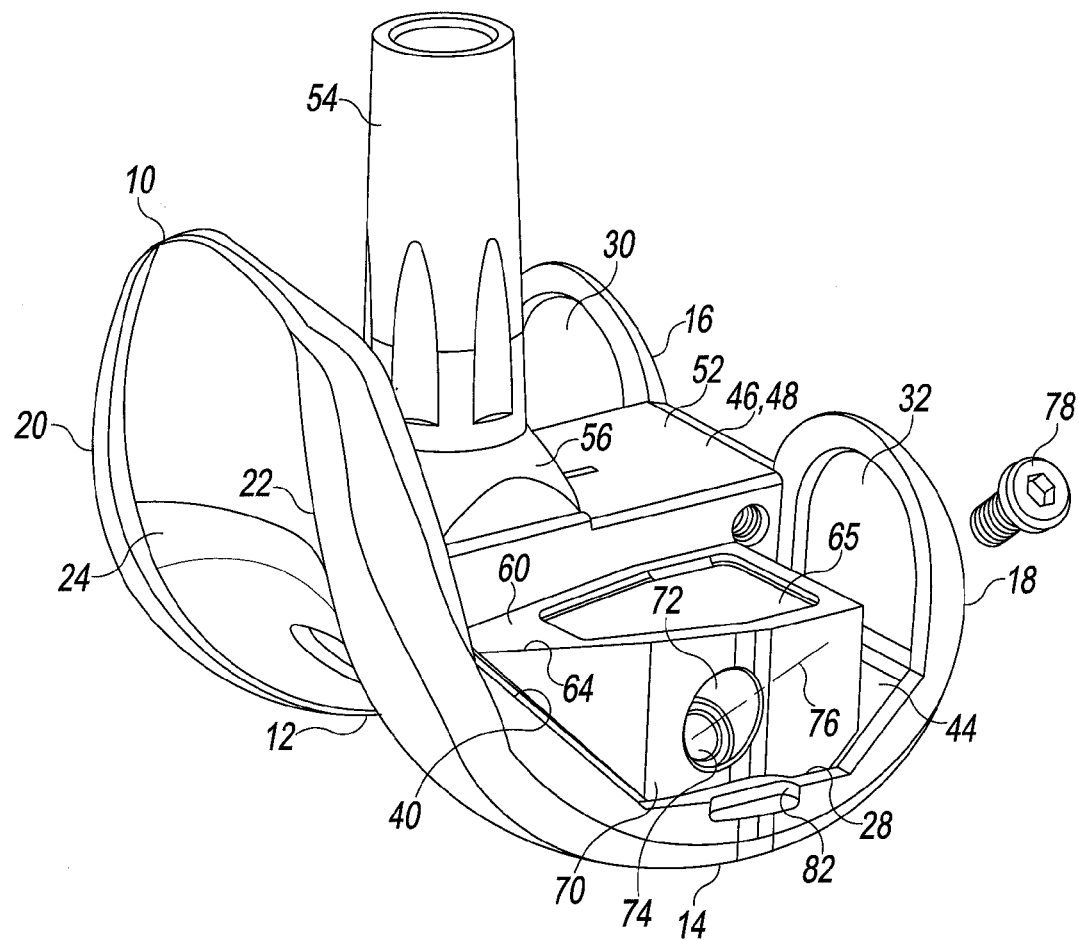
FIG. 8 is a perspective view showing the distal femoral articulation component of FIGS. 1-3 with the distal augment of FIGS. 4-7 shown in place on the distal bone-facing surface of the distal femoral articulation component and also showing a connector for securing the distal augment to the distal femoral articulation component.
Figure 9:
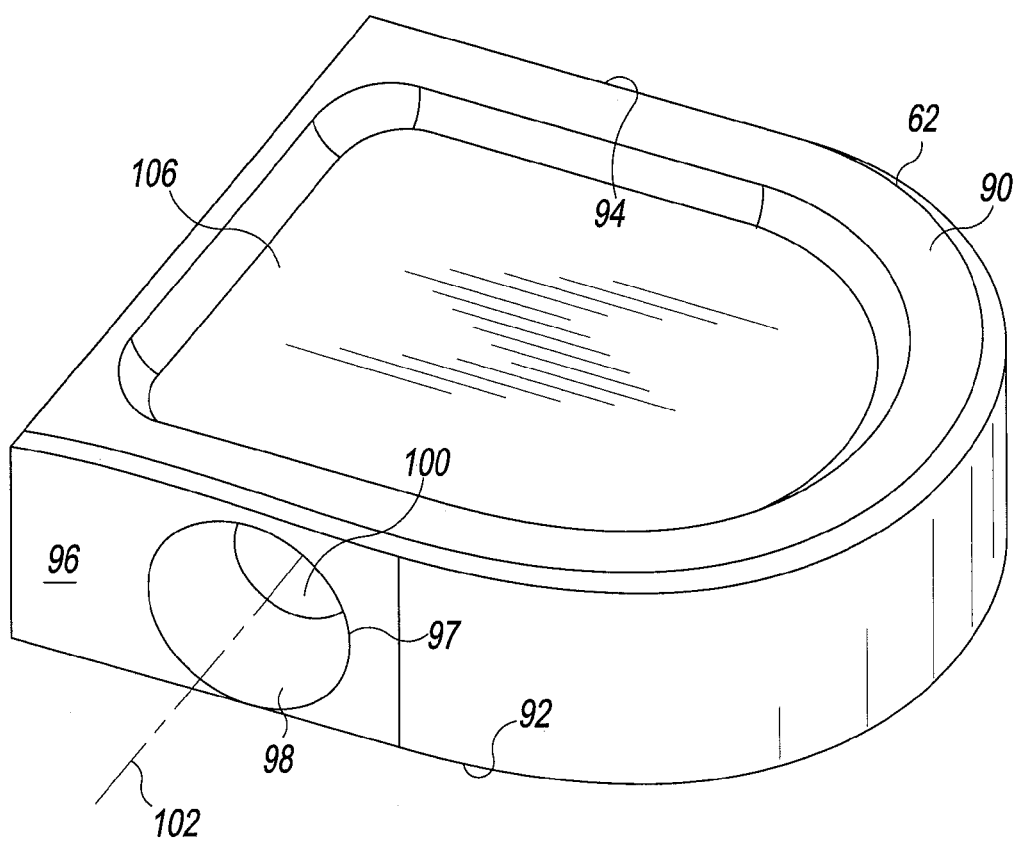
FIG. 9 is a perspective view of a posterior augment of a modular knee prosthesis system incorporating the principles of the present invention.
Figure 10:
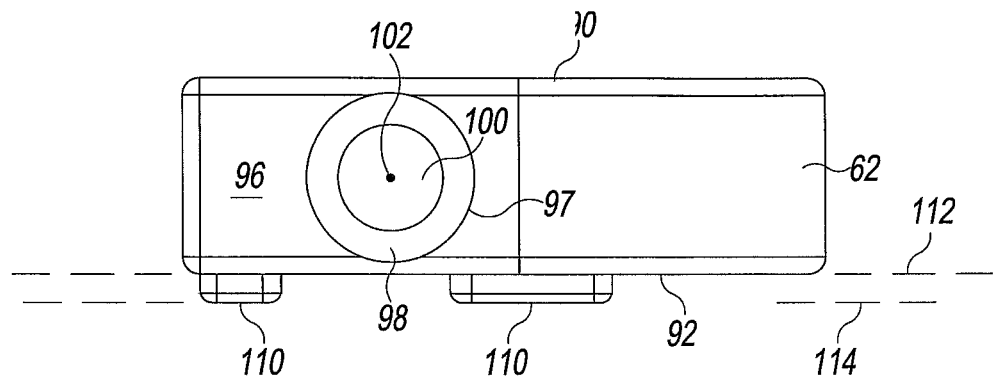
FIG. 10 is a side view of the posterior augment of FIG. 9.
Figure 11:
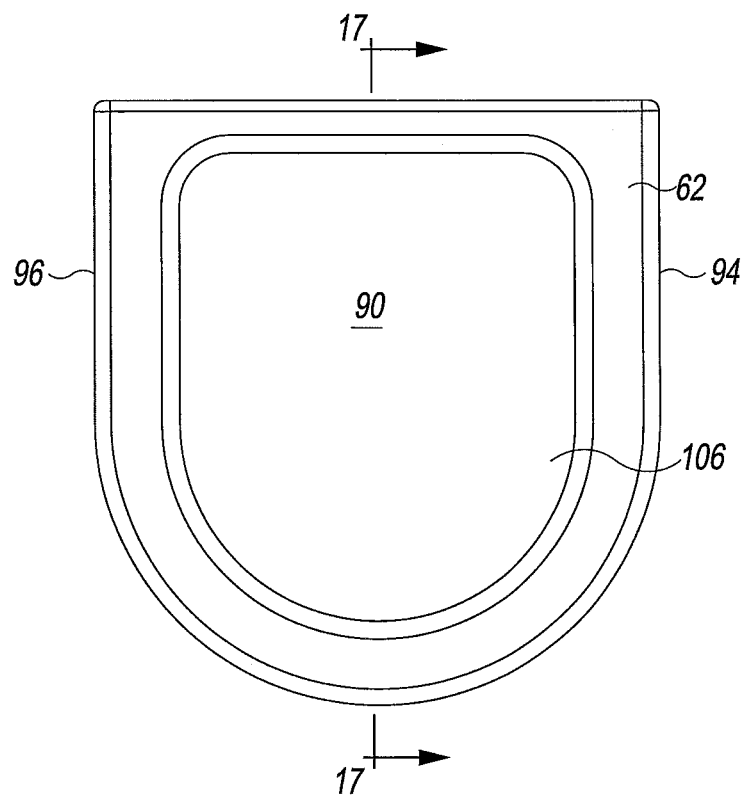
FIG. 11 is a top view of the posterior augment of FIGS. 9-10.
Figure 12:
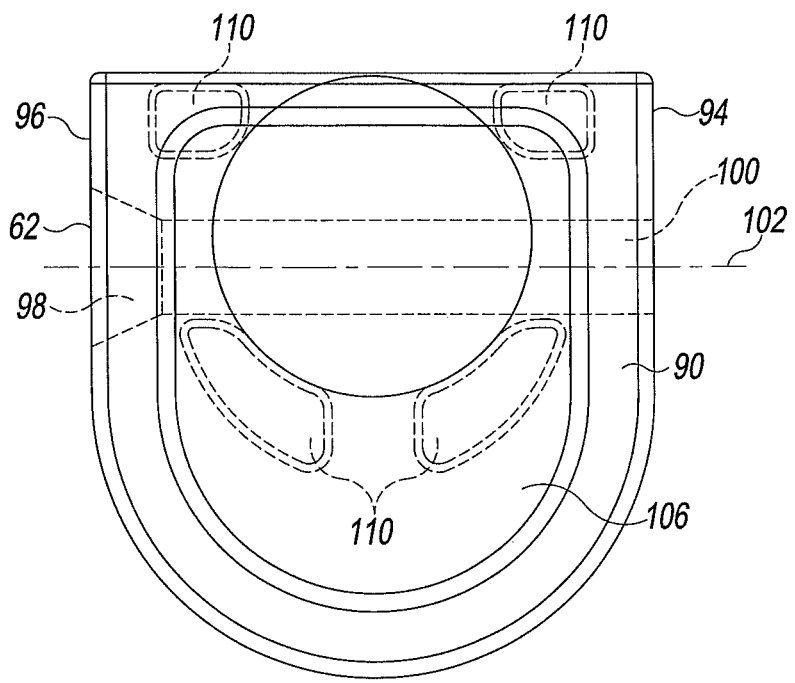
FIG. 12 is a top view of the posterior augment of FIGS. 9-11, with additional features shown in phantom.
Figure 13:
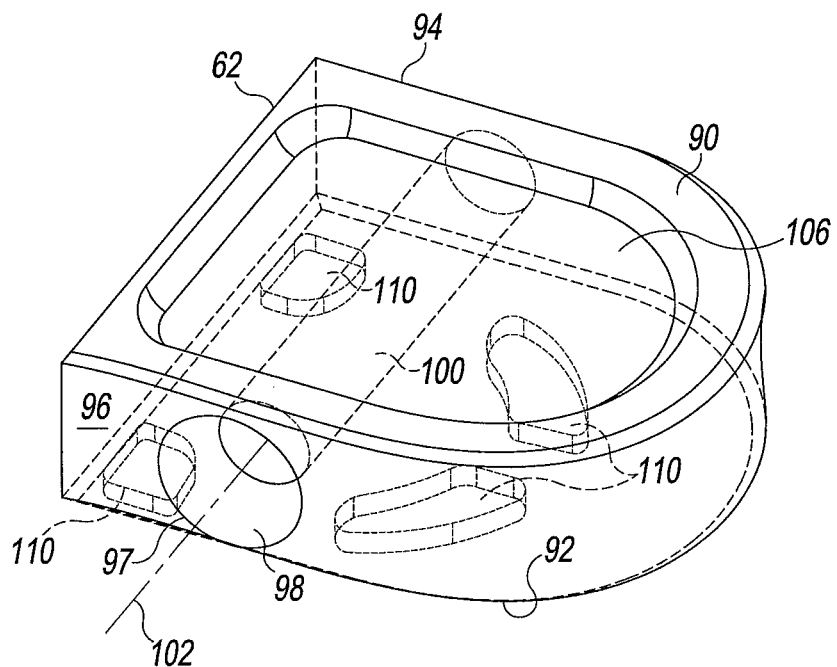
FIG. 13 is a perspective view of the posterior augment of FIGS. 9-12, with additional features shown in phantom.
Figure 15:
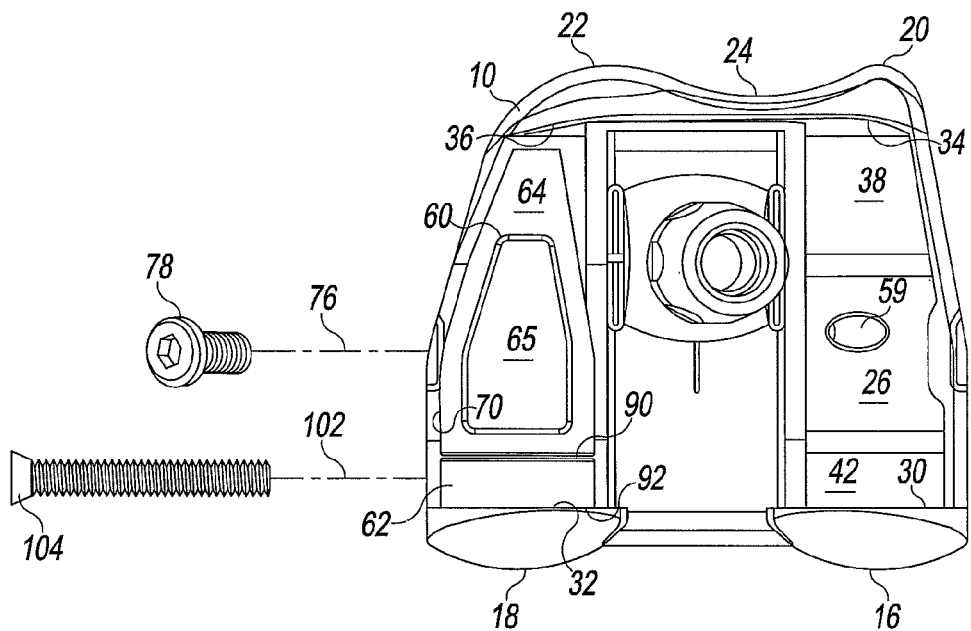
FIG. 15 is a top view showing the distal femoral articulation component of FIGS. 1-3 with the distal augment of FIGS. 4-7 and posterior augment of FIGS. 9-13 shown in place on the distal and posterior bone-facing surfaces of the distal femoral articulation component and also showing connectors for securing the distal and posterior augments to the distal femoral articulation component.
Figure 16:
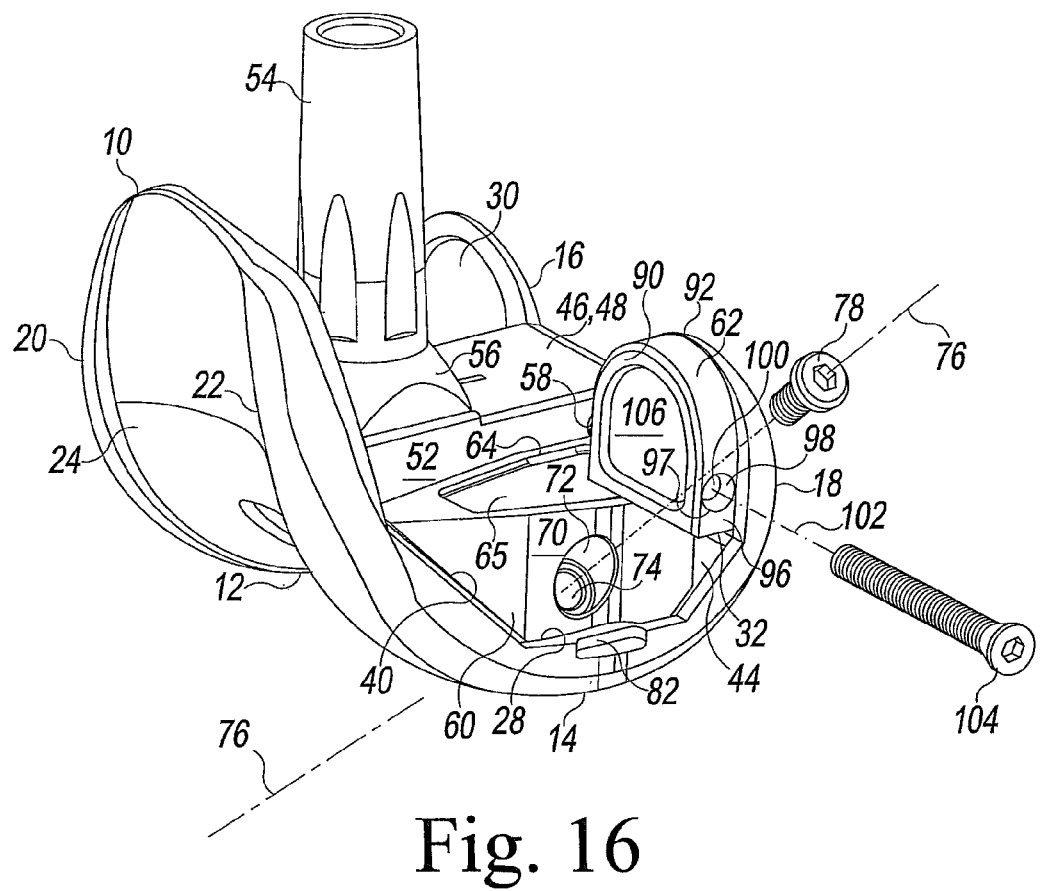
FIG. 16 is a perspective view of the components of FIG. 15.

The screw or bolt 78 may be used to secure the distal femoral augment 60 to the distal femoral articulation component 10 by placing the second surface 66 of the distal augment 60 against the distal bone-facing surface 26 or 28, as shown in FIGS. 8 and 15-16. The screw 78 is inserted through the hole 72 and bore 74 along the axis 76 and the threaded end of the screw 78 is threaded into the opening 72 and threaded bore 74 and tightened to secure the elements 10, 60 together. The surgeon can accomplish all of these tasks from the medial or lateral side; it is not necessary to align a screw or screwdriver along a generally superior-inferior axis to connect the augment 60 to the distal femoral articulation component 10.

It should be understood that the side of the augment 60 including the hole or opening 72 and bore 74 could be either the medial or lateral side of the augment. Moreover, the distal augment 60 could be made symmetrical about an anterior-posterior plane with openings and bores provided on each side of a single augment, one on the medial side and one on the lateral side to define a universal distal augment. Such a universal distal augment could be selectively used on either the medial or lateral condyle of the distal femoral articulation component. In addition, although the illustrated embodiment illustrates a single hole and bore on one side of the distal augment, it should be understood that multiple holes and bore could be provided on one or more sides of the augment. Moreover, in the case of holes and bores being provided on more than one side of the augment, or multiple holes and bores provided on the augment, one or more plugs could be provided to fill the used holes.

Figure 20:
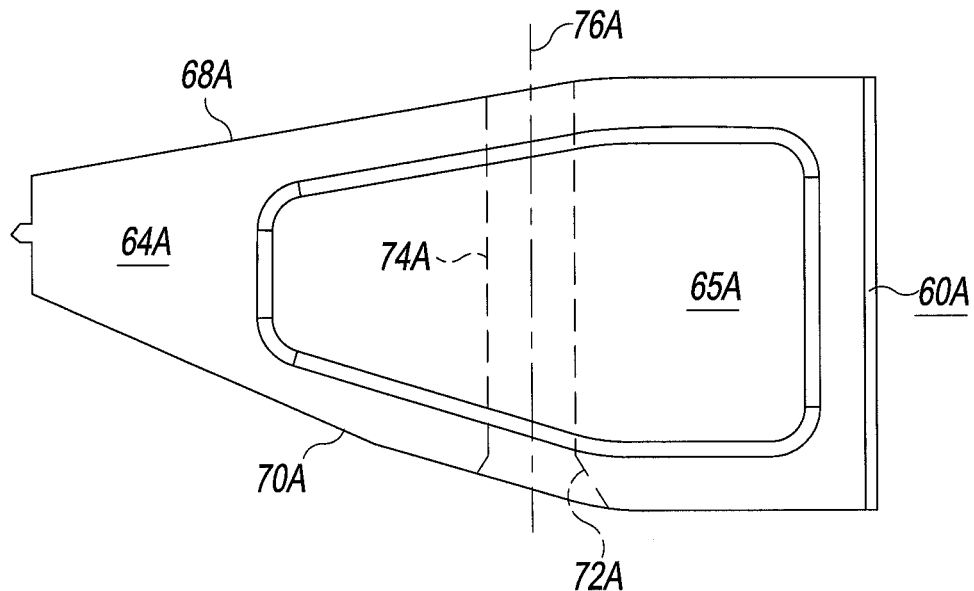
FIG. 20 is a top view of an alternative embodiment of a distal augment.
Figure 21:
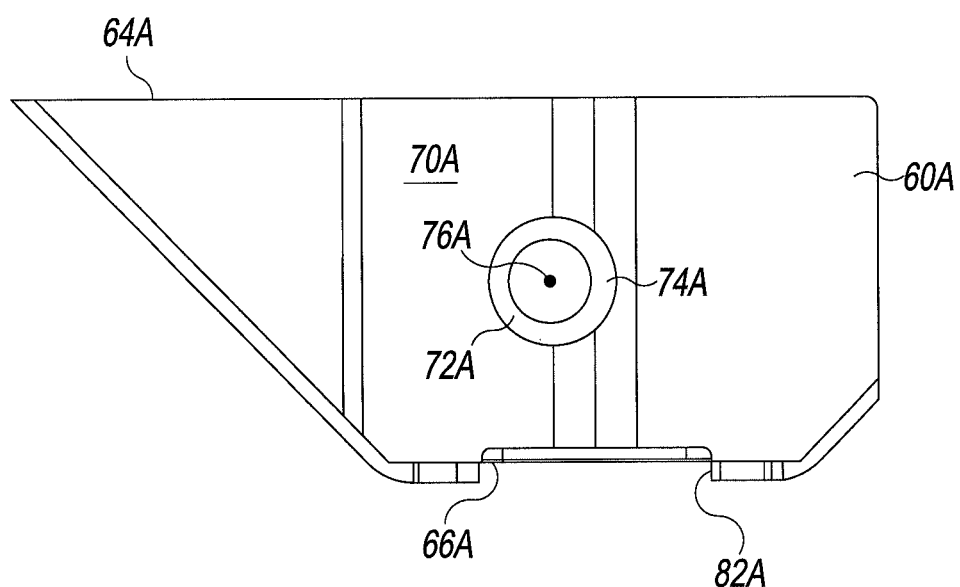
FIG. 21 is a side view of the distal augment of FIG. 20.

An alternative embodiment of the distal augment is illustrated in FIGS. 20-21, where elements similar to those described above are identified with the same reference numbers used for FIGS. 4-7, followed by the designation "A". The embodiment of FIGS. 20-21 differs from that of FIGS. 4-7 in that the cylindrical bore 74A extends from the side surface 70A, through the body of the augment 60A and out through the opposite side surface 68A of the augment 60A. The bore 74A has a central longitudinal axis 76A that lies between the first surface 64A and the second surface 66A of the augment 60A. The interior of the cylindrical bore 74A is smooth, and sized to receive the shaft of a connector. The side walls 50, 52 of the box 46 may have threaded bores (not shown), similar to bore 58 but sized, shaped and positioned to receive the connector to assemble the distal augment 60A and the distal femoral articulation component 10 together.

The first and second surfaces 64, 64A, 66, 66A of the distal femoral augment 60, 60A may include additional features. For example, the first surface 64, 64A which faces the resected bone surface, may include a recess defining a cement pocket, shown at 65 in FIGS. 4-5, 7-8 and 15-16 and 65A in FIG. 20. The second surface 66, 66A which faces the distal bone-facing surface 26 or 28 of the distal femoral articulation component 10, may include a plurality of raised feet to stabilize and locate the augment 60 on the distal femoral articulation component 10; such feet are shown in phantom at 80 in FIG. 7. The outermost surfaces of the illustrated feet 80 are shaped to rest upon the surface of the cement pocket 65 in the distal bone-facing surface 26 or 28.

Both side surfaces 68, 68A, 70, 70A of the augment 60, 60A may also include features to facilitate grasping the augment with a tool, such as recesses shown at 82 in FIGS. 4, 7-8 and 16 and 82A in FIG. 21.

The anterior portion of the distal femoral augment 60, 60A is shaped to fit against the anterior chamfer surface 38 or 40 of the distal femoral articulation component 10. The anterior-posterior length of the distal femoral augment 60, 60A allows for a space between the posterior-most end of the augment 60, 60A and the posterior bone-facing surface 30 or 32 of the distal femoral articulation component 10 to allow for a part of the posterior femoral augment 62 to be received between the distal femoral augment 60, 60A and the posterior bone-facing surface 30 or 32.

Turning next to the posterior femoral augment 62, the posterior femoral augment 62 has a first surface 90, a second surface 92 spaced from and generally opposite to the first surface 90 and side surfaces 94, 96 extending between the first surface 90 and the second surface 92. The posterior femoral augment 62 has a body extending between the surfaces 90, 92, 94, 96.

One of the side surfaces 94 or 96 of the posterior femoral augment 62 has a circular opening 97 into a tapered countersink 98 and cylindrical bore 100. The bore 100 extends from one side surface to the other and has a central longitudinal axis 102 that runs between the first and second surfaces 90, 92. The interior of the cylindrical bore 100 is smooth, and sized to receive the shaft of a second connector 104. In the illustrated embodiment, the second connector 104 comprises a screw or bolt having a length greater than the medial-lateral dimension of the posterior femoral augment 62 so that the screw may be inserted through the opening 97 and bore 100 to engage the threads in the bore 58 in the side wall 52 of the femoral box 46.

Figure 14:
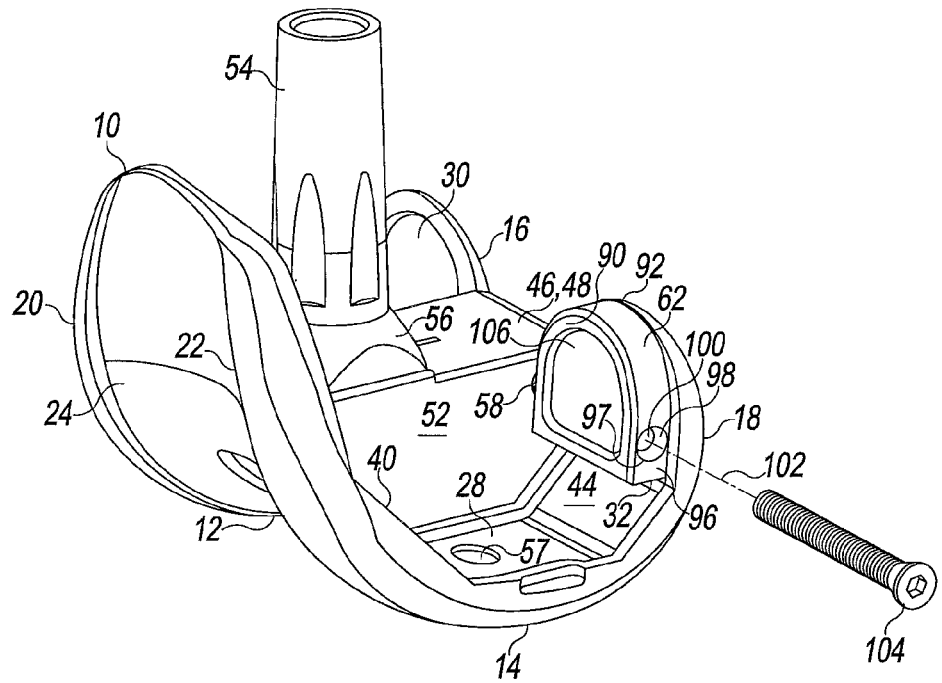
FIG. 14 is a perspective view showing the distal femoral articulation component of FIGS. 1-3 with the posterior augment of FIGS. 9-13 shown in place on the posterior bone-facing surface of the distal femoral articulation component and also showing a connector for securing the posterior augment to the distal femoral articulation component.

The second connector 104 may be used to secure the posterior femoral augment 62 to the distal femoral articulation component 10 by placing the second surface 92 of the posterior augment 62 against the posterior bone-facing surface 30 or 32, as shown in FIGS. 14-16. The second connector 104 is inserted through the hole 97 and bore 100 along the axis 102 and the threaded end of the second screw connector 104 is received into the opening and engages the threads of the bore 58 in the side wall 50 or 52 of the femoral box 46. The connector 104 is tightened to secure the elements 10, 62 together. The surgeon can accomplish all of these tasks from the medial or lateral side; it is not necessary to align a screw or screwdriver along a generally anterior-posterior axis to connect the posterior augment 62 to the distal femoral articulation component 10.

Alternatively, the bore 100 could be oriented to extend from one of the side surfaces 94 or 96 to the posterior surface 92 and into a bore formed in one of the posterior bone facing surfaces 30 or 32, similar to the bore 74 in the first illustrated distal femoral augment 60. In addition, other types of connectors (such as pins and collets) could be used.

Figure 17:
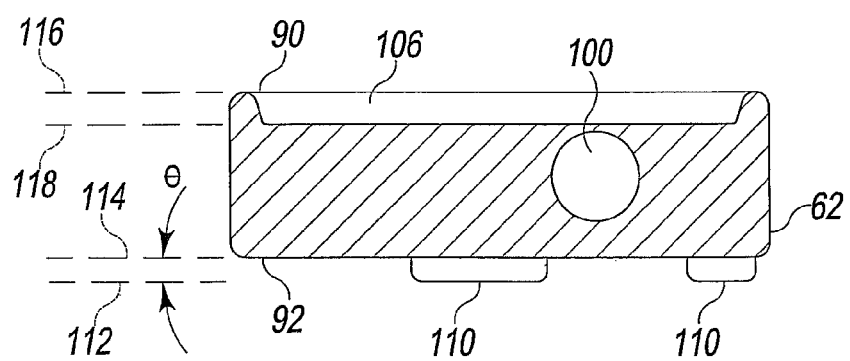
FIG. 17 is a cross-section of the posterior augment of FIGS. 9-13 taken along line 17-17 of FIG. 11.
Figure 18:
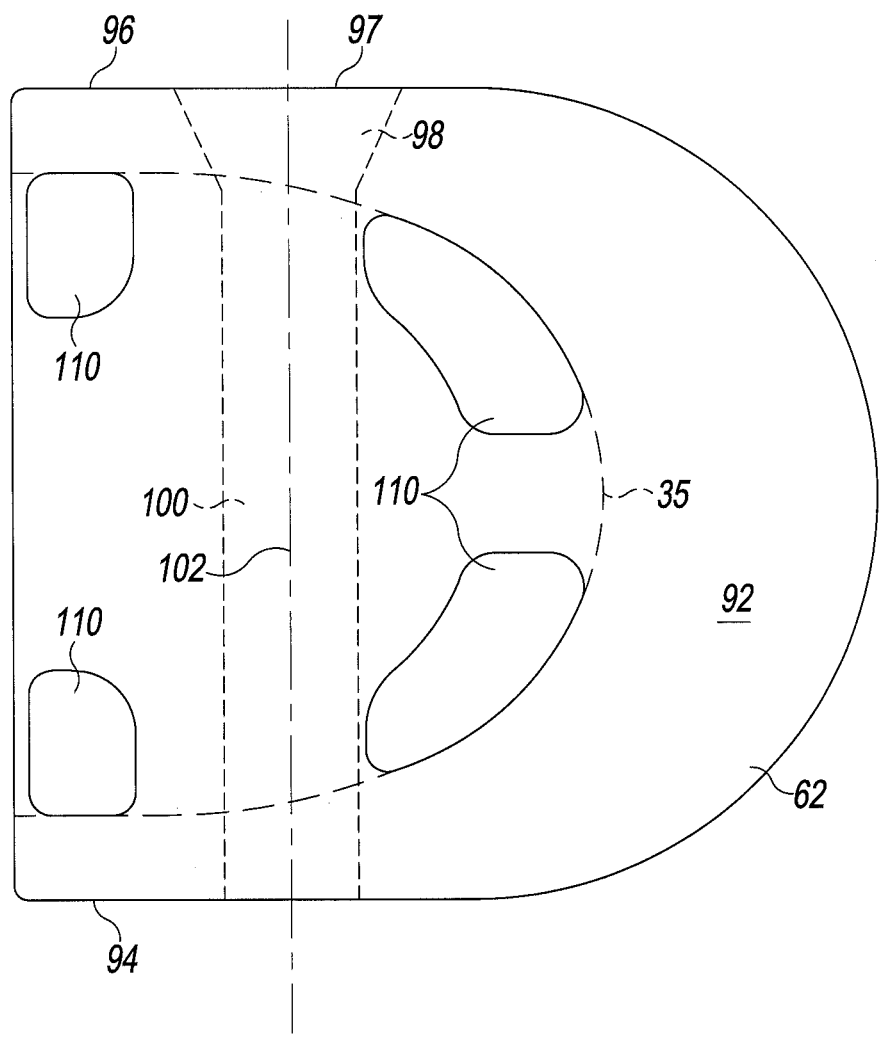
FIG. 18 is a bottom plan view of the posterior augment of FIGS. 9-13 and 17, with the outline of the posterior cement pocket of the distal femoral articulation component shown in phantom.
Figure 19:
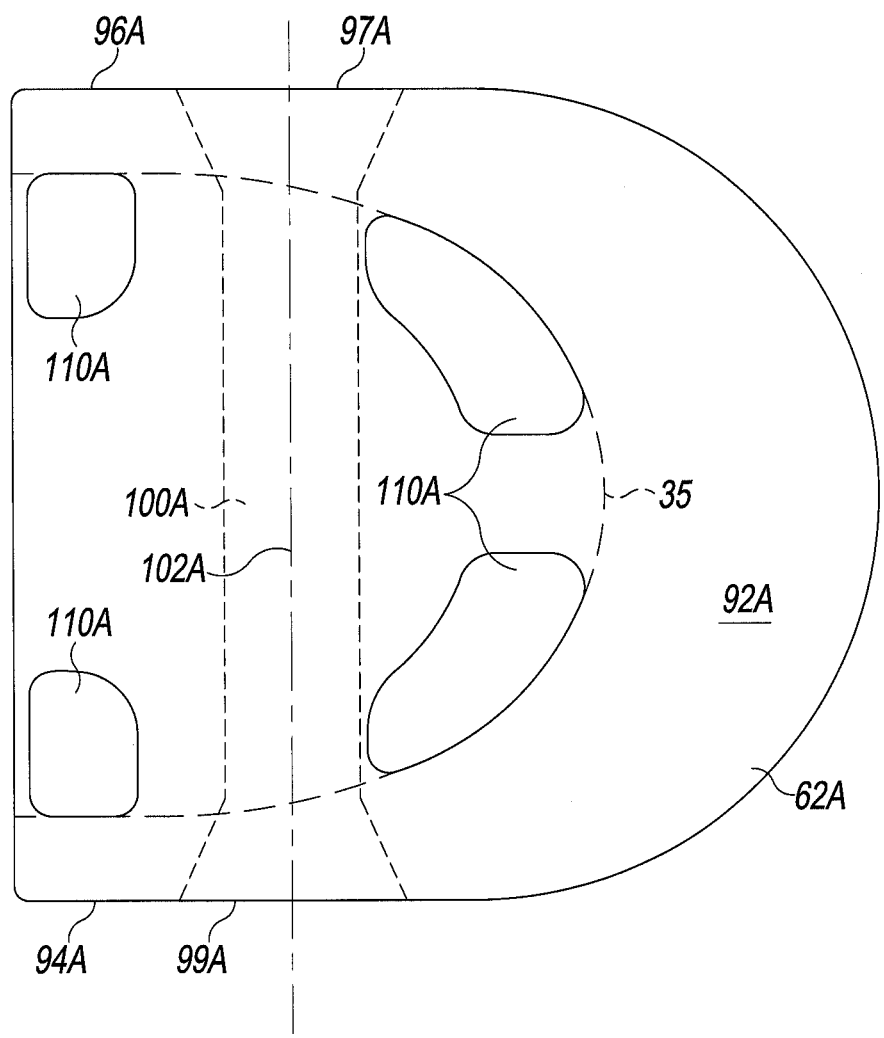
FIG. 19 is a view similar to FIG. 18, showing an alternative embodiment of the posterior augment that is universal, that is, that can be selectively used on either the medial or lateral side of the distal femoral articulation component.
Figure 22:
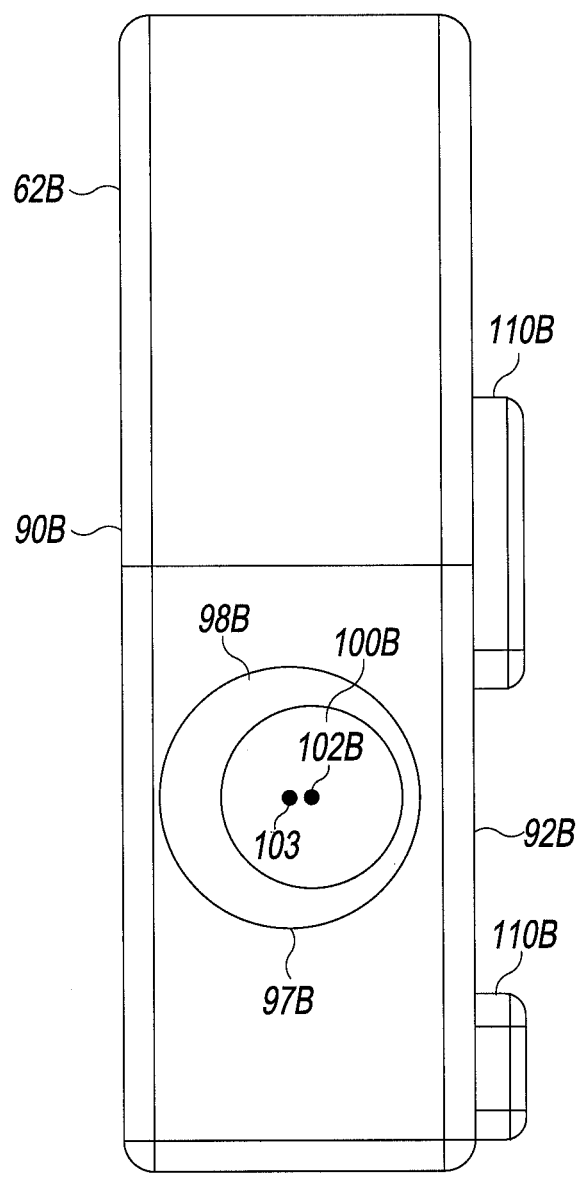
FIG. 22 is a side view of the posterior augment, similar to FIG. 9 but incorporating an additional feature.

The posterior augment illustrated in FIGS. 9-18 is asymmetrical about a superior-inferior plane, although the augment could be symmetrical. A symmetrical design is shown in FIG. 19, with parts similar to those described above for the asymmetrical design labeled with the same reference number, followed by the designation "A". The symmetrical design, shown in FIG. 19, is substantially identical to the asymmetrical design, differing only in that both side surfaces 94A, 96A have the same size opening 97A, 99A leading into the bore 100A, and both ends of the bore 100A have tapered countersinks 98A, 101A. With the design of FIG. 19, the same posterior augment 62A could be used on either the medial or lateral condyle of the distal femoral articulation component. In addition, multiple holes and bores could be provided on each side of the posterior augment. If multiple holes are provided, plugs may be provided to fill unused holes. Another embodiment of a posterior augment illustrated in FIG. 22, with parts similar to those described above for the above posterior augment designs 62, 62A labeled with the same reference number, followed by the designation "B". In the embodiment of FIG. 22, the bore 100B has a central longitudinal axis 102B and the counterbore or counter-sink 98B has a different central longitudinal axis 103 offset from the central longitudinal axis 102B of the bore 100B. With this embodiment, the shaft of the screw or bolt may have a diameter smaller than the diameter of the bore 100B and the head of the bolt may have a diameter smaller than the diameter of the counterbore 98B so that the surgeon has more play in the position of the augment 62B when first assembling the components; as the bolt is tightened, the head of the screw or bolt will ultimately fit within the portion of the counterbore 98B immediately surrounding the bore 100B and the augment 62B will be held tightly against the posterior bone-facing surface 30 or 32 of the femoral articulation component.

The first and second surfaces 90, 90A, 90B, 92, 92A, 92B of the posterior femoral augment 62, 62A, 62B may include additional features. For example, the first surface 90, 90A, 90B which faces the resected bone surface, may include a recess defining a cement pocket, shown at 106 in FIGS. 9 and 11-14 and 16. The second surface 92, 92A, 92B which faces the posterior bone-facing surface 30 or 32 of the distal femoral articulation component 10, may include a plurality of raised feet to stabilize and locate the augment 62 on the distal femoral articulation component 10; such feet are shown at 110 in FIG. 10, in phantom in FIGS. 12-13, at 110A in FIG. 19 and at 110B in FIG. 22. The outermost surfaces of the feet 110, 110A, 110B are shaped to rest upon the surface of the cement pocket 33 or 35 in the posterior bone-facing surface 30 or 32.

If the cement pocket 35 or 37 is tapered so that the pockets are deeper at their inferior ends than at their superior ends, the feet 110, 110A, 110B may be shaped so that the posterior-most surfaces of the feet lie in a plane 112 that defines an angle θ with the plane 114 parallel to the plane 116 along the anterior-most portions of the first surface 90 of the posterior augment 62, as shown in FIG. 17. The angle θ may vary according to the corresponding taper angle in the cement pocket 35 or 37. It should be understood that if the cement pocket 33 or 35 in the distal femoral articulation component 10 is not tapered, planes 112, 114 and 116 may all be parallel to each other. It should also be understood that the same principles may be applied to the feet 80 of the distal augment 60.

FIG. 17 also illustrates the cement pocket 106 in the first surface 90 of the posterior augment. In FIG. 17, the posterior-most surface of the cement pocket 106 lies in a plane 118. In the illustrated embodiment, plane 118 is parallel to planes 114 and 116, although it should be understood that the principles of the invention disclosed in U.S. Pat. Pub. No. 20120083894, entitled "Femoral Component of a Knee Prosthesis Having an Angled Cement Pocket", may be applied to the cement pocket 106, with the plane 118 defining an acute angle with the planes 114, 116. Although not illustrated, the same angular relationships may be used for cement pocket 65 in the distal augment 60.

Although locating feet, such as feet 80, 110, 110A, 110B are optional, if used, it may be advantageous to shape and position the feet so that the edges of the feet contact edges of the rims in the surfaces 26, 28, 30, 32 defining the distal and posterior cement pockets 31, 33, 35, 37. FIGS. 18-19 illustrate a plurality of feet 110 shaped and positioned to fit in a unique position within the cement pocket to positively locate the posterior augment 62 within the cement pocket (an example of the outline of the cement pocket being shown in phantom at 35) of the distal femoral articulation component 10. Although not illustrated, it should be understood that the feet 80 of the distal augment 60 may be shaped and positioned to fit in a unique position to positively locate the distal augment 60 within the distal cement pockets 31, 33.

A typical surgical kit would include a variety of sizes of distal femoral augments 60, 60A and posterior femoral augments 62, 62A, 62B to provide the surgeon with a choice among various thicknesses of augments. For example, both types of augments could be provided with thicknesses increasing by 2 mm for each size of augment. Since distal femoral articulation components are commonly provided in a variety of sizes, a group of augments of different thicknesses may be provided for use with each size of distal femoral articulation component in the kit.

In use, the augments 60, 60A, 62, 62A, 62B may be used with the distal femoral articulation component 10 to address bony deficiencies and in situations where placing the articulation component 10 directly on the resected bone would result in an undesirable position of the articulation surfaces 12, 14; that is, the joint line defined by the articulation between the femoral articulation surfaces 12, 14 and the articulation surfaces of the proximal tibial component may be elevated. Elevation of the joint line may adversely affect performance of the prosthetic knee system: the positions of the collateral ligament attachments to the femur relative to the joint line may impact knee kinematics, the articulation of the patella against the femoral component will be impacted, and the function of the extensor mechanism will also be impacted. To distalize the joint line and to compensate for inadequate bone at the distal femur, the surgeon may opt to use the distal augments of the present invention along with the posterior augments to property position the femoral articulation surfaces in both extension and flexion. Various combinations of thicknesses of distal and femoral augments 60, 60A, 62, 62A, 62B may be used to optimize the assembly for the needs of the individual patient.

The distal augment 60, 60A, may be assembled with the distal femoral articulation component 10 intraoperatively, by inserting a connector 78 through the bore 74, 74A along axis 76, 76A in the distal femoral augment 60, 60A and into the opening 57 or 59 in the distal bone-facing surface 26 or 28 of the distal femoral articulation component 10. Similarly, connector 104 may be inserted through the bore 100, 100A, 100B in the posterior femoral augment 62, 62A, 62B and into opening 58 (or the equivalent opening on the opposite side of the femoral box 46) in the femoral box 46 of the distal femoral articulation component 10. The location and orientation of the openings 57, 58, 59, 72, 72A, 97, 97A, 97B and bores 74, 74A, 100, 100A, 100B allow for the components 10, 60, 60A, 62, 62A, 62B to be assembled with standard tools. The assembly may then be cemented into place on the distal femur by placing an appropriate cement in the cement pockets 65, 65A, 106 of the augments 60, 60A, 62, 62A, 62B. The connectors 78, 104 remain accessible from either the medial or lateral side after implantation.

Since the connectors 78, 104 remain accessible post-implantation, revision of the distal femoral implant is facilitated. The surgeon may use a standard tool to remove the connectors 78, 104 from either the medial or lateral side while the assembly remains on the femur to sever the connections between the augments 60, 60A, 62, 62A, 62B and the distal femoral articulation component 10. Once these connections are severed, the distal femoral articulation component 10 may be readily removed (following separation of the anterior bone-facing surfaces 34, 36 of the distal femoral articulation component 10 from the adjacent bone surface, such as by running a saw blade through the cement mantle along the anterior bone-facing surfaces 34, 36). The surgeon may then readily cut through the cement mantle between the augments 60, 62 and the bone to remove the augments 60, 60A, 62, 62A, 62B from the bone.

All of the components of the illustrated implant system may be made of standard materials, such as standard metals (such as titanium alloys and cobalt-chromium alloys) for the augments 60, 60A, 62, 62A, 62B and distal femoral articulating component 10.

It will be noted that alternative embodiments of each of the systems of the present disclosure may not include all of the features described yet still benefit from at least some of the advantages of such features. Those of ordinary skill in the art may readily devise their own implementations of a system that incorporates one or more of the features of the present disclosure and fall within the spirit and scope of the invention as defined by the appended claims.

We claim:

1. A modular knee prosthesis system comprising:
   a distal femoral articulation component having a pair of curved distal condylar articulating surfaces, a pair of curved posterior condylar articulating surfaces, a distal bone-facing surface, a posterior bone-facing surface and a pair of openings;
   a distal augment sized and shaped to be received on the distal bone-facing surface of the distal femoral articulation component, the distal augment including a first surface, a second surface spaced from and generally opposite to the first surface and side surfaces extending between and connecting the first surface and the second surface, a body between the first and second surface, at least one of the side surfaces having an opening into a bore extending from the side surface through the body and through the second surface of the distal augment;
   a posterior augment sized and shaped to be received on the posterior bone-facing surface of the distal femoral articulation component, the posterior augment including a first surface, a second surface spaced from and generally opposite to the first surface and side surfaces extending between and connecting the first surface and the second surface, a body between the first and second surface, at least one of the side surfaces having an opening into a bore extending from the side surface through the body and through the other side surface of the posterior augment;
   a first connector extending through the bore of the distal augment and into one of the openings in the distal femoral articulation component to connect the distal augment to the distal femoral articulation component; and
   a second connector extending through the bore of the posterior augment and into the other opening in the distal femoral articulation component to connect the posterior augment to the distal femoral articulation component.

2. The modular knee prosthesis system of claim 1 wherein the bore in the distal augment has a central longitudinal axis defining an acute angle with the second surface.

3. The modular knee prostheses system of claim 2 wherein:
   one of the openings in the distal femoral articulation component is in the distal bone-facing surface of the distal femoral articulation component;
   the opening in the distal bone-facing surface is positioned and shaped to align with the bore in the distal augment when the second surface of the distal augment is mounted on the distal bone-facing surface of the distal femoral articulation component.

4. The modular knee prosthesis of claim 1 wherein the distal femoral articulation component is a posterior stabilized component including:
   a box having a box top wall and a box side wall, the box side wall extending from the box top wall to at least one of the distal bone-facing surface and a posterior bone-facing surface of the distal femoral articulation component; and
   wherein one of the openings in the distal femoral articulation component is in the box side wall.

5. The modular knee prosthesis of claim 4 wherein the bore in the posterior augment has a central longitudinal axis between the first surface and the second surface of the posterior augment.

6. The modular knee prostheses system of claim 5 wherein:
   the opening in the box side wall is positioned and shaped to align with the bore in the posterior augment when the second surface of the posterior augment is mounted on one of the bone-facing surfaces of the distal femoral articulation component.

7. The modular knee prosthesis system of claim 4 wherein the bore in the distal augment has a central longitudinal axis defining an acute angle with the second surface of the distal augment.

8. The modular knee prosthesis system of claim 1 wherein the second connector is longer than the first connector.

9. The modular knee prosthesis system of claim 1 wherein:
   the distal bone-facing surface of the distal femoral articulation component has a recessed distal cement pocket;
   the posterior bone-facing surface of the distal femoral articulation component has a recessed posterior cement pocket;
   the second surface of the distal augment includes a plurality of protruding feet sized, shaped and positioned to be received in a unique position within the distal cement pocket when the distal augment is assembled with the distal femoral articulation component to positively locate the distal augment with respect to the distal cement pocket; and
   the second surface of the posterior augment includes a plurality of protruding feet sized, shaped and positioned to be received in a unique position within the posterior cement pocket when the posterior augment is assembled with the distal femoral articulation component to positively locate the posterior augment with respect to the posterior cement pocket.

10. The modular knee prosthesis system of claim 9 wherein:
    the recessed posterior cement pocket is tapered so that the posterior cement pocket is deeper at one end; and the feet of the posterior augment are shaped so that the outermost surfaces of the feet lie in a plane that defines an acute angle with the first surface of the posterior augment.

11. The modular knee prosthesis of claim 1 wherein:

the first surface of the distal augment has a recessed cement pocket; and the first surface of the posterior augment has a recessed cement pocket.

* * * * *